(12) United States Patent
Amornsiripanitch

(10) Patent No.: US 6,389,150 B1
(45) Date of Patent: May 14, 2002

(54) TOTAL QUALITY OF HAIR PARAMETERS MEASURING METHOD

(76) Inventor: Somnuk Amornsiripanitch, 32/319 Chaengwattana Street, Nonthaburee (TH), 11120

( * ) Notice: Subject to any disclaimer, the term of this patent is extended or adjusted under 35 U.S.C. 154(b) by 0 days.

(21) Appl. No.: 09/325,345

(22) Filed: Jun. 4, 1999

(30) Foreign Application Priority Data

Mar. 22, 1999 (TH) ................................................ 049437

(51) Int. Cl.[7] ................................................ G06K 9/00
(52) U.S. Cl. ................................. 382/100; 382/128
(58) Field of Search .................................. 382/100, 128, 382/129, 133, 181, 192, 206, 218, 221; 33/512; 601/7

(56) References Cited

U.S. PATENT DOCUMENTS

| | | | | |
|---|---|---|---|---|
| 4,170,827 A | * | 10/1979 | Katz et al. ..................... | 33/712 |
| 4,807,163 A | | 2/1989 | Gibbons ...................... | 202/19 |
| 6,099,870 A | * | 8/2000 | Cauwenbergh ............. | 424/702 |
| 6,121,269 A | * | 9/2000 | Henry et al. ................ | 514/259 |
| 6,162,211 A | * | 12/2000 | Tankovich et al. ............. | 606/9 |
| 6,333,193 B1 | * | 12/2001 | Shiba ........................ | 435/405 |

* cited by examiner

Primary Examiner—Andrew W. Johns
Assistant Examiner—Shervin Nakhjavan
(74) Attorney, Agent, or Firm—Pennie & Edmonds LLP

(57) ABSTRACT

A method of measuring hair quality in a predefined area of the scalp. The method addresses the preparation of the scalp and the process for measuring the density, the size of hair shaft, the length of each hair growing out from the area. A video capture device capable of storing images transferred from a camera, computer hardware and software capable of archiving the images and measuring the size and length of each hair shaft in the images. A method of dying hair shafts combined with above image processing techniques will provide measure of almost every phases of hair cycle. The end result will be the statistical data of the ratio of growing hairs and non-growing hairs with the average of hair growth rates and other data such as the maximum and minimum growth rate, the standard error, the variance etc.

23 Claims, 4 Drawing Sheets

TOTAL QUALITY OF HAIR PARAMETERS MEASURING METHOD

BACKGROUND OF THE INVENTION

1. Field of the Invention

Figure 1:
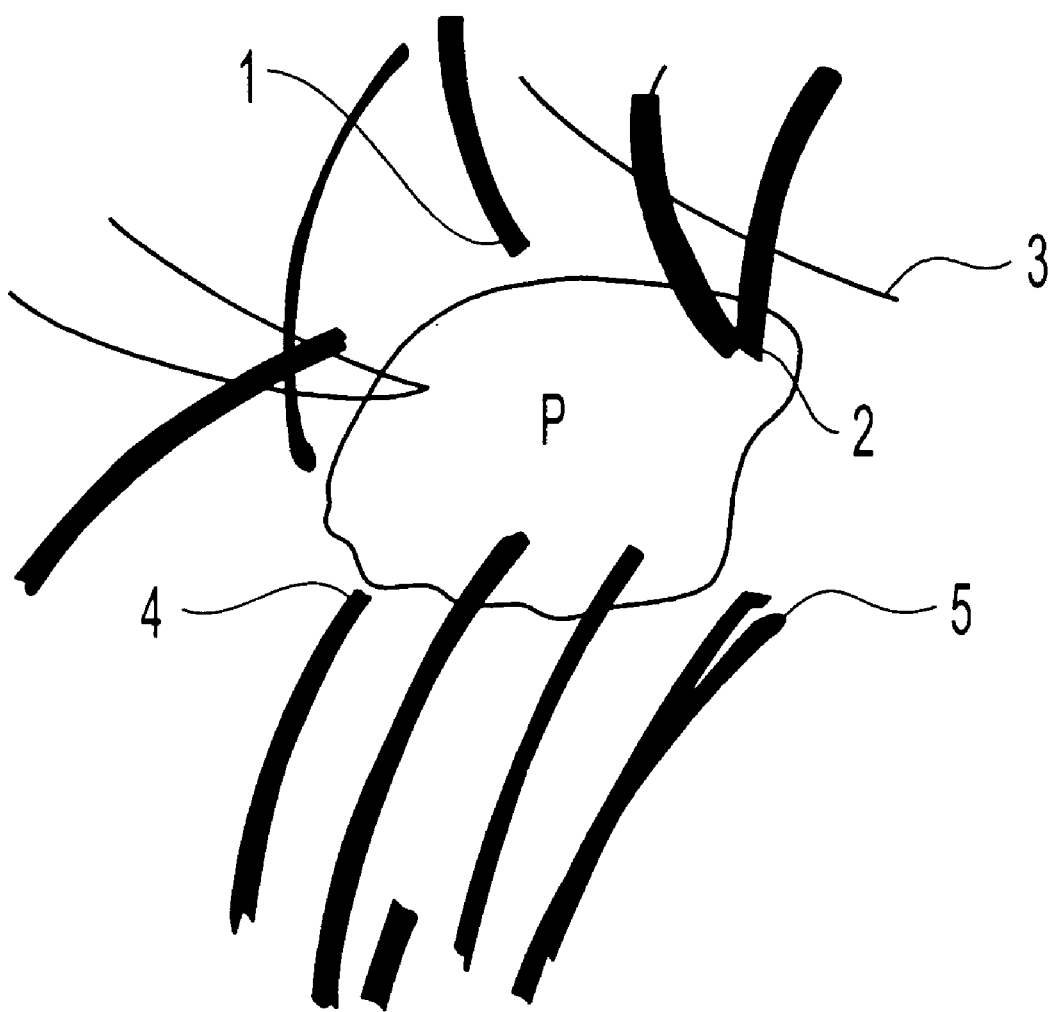
Figure 2:
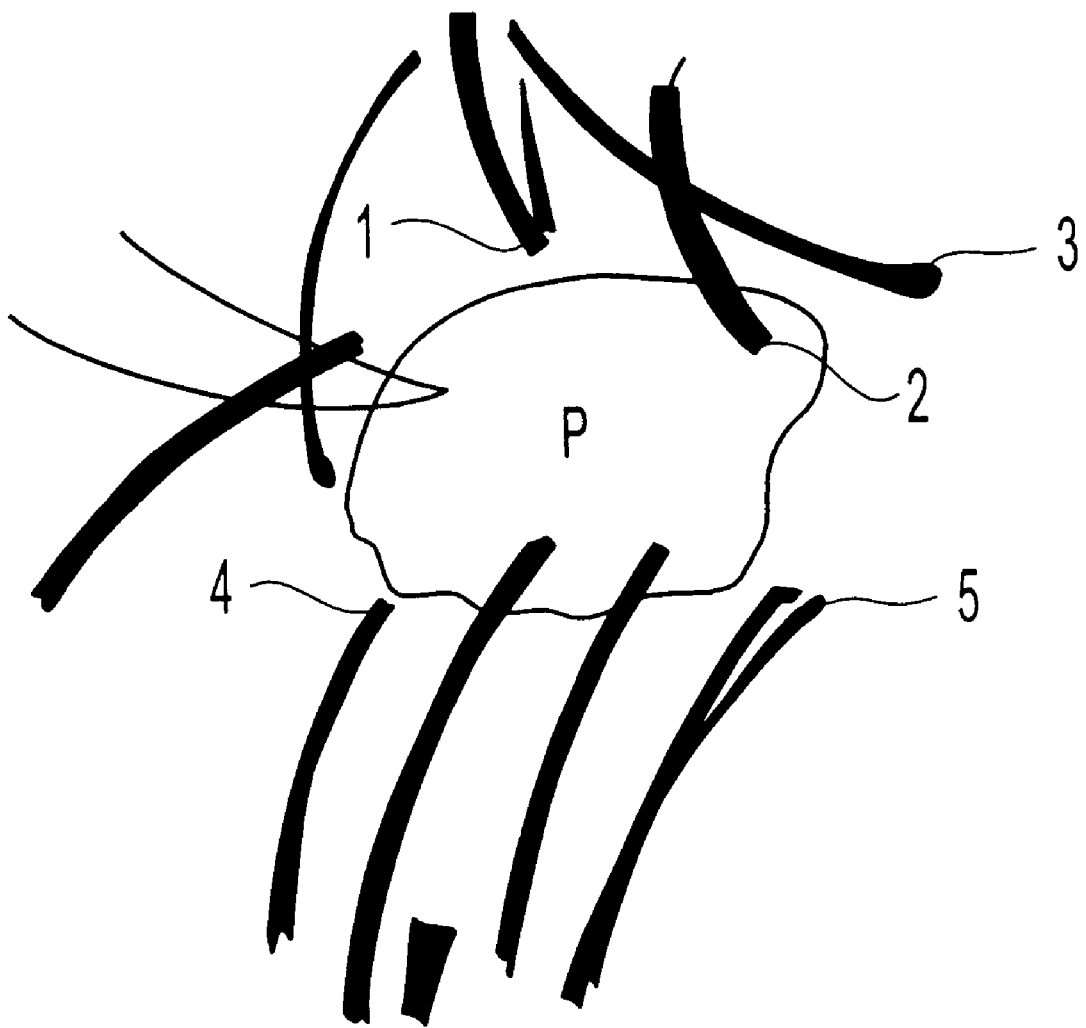
Figure 3:
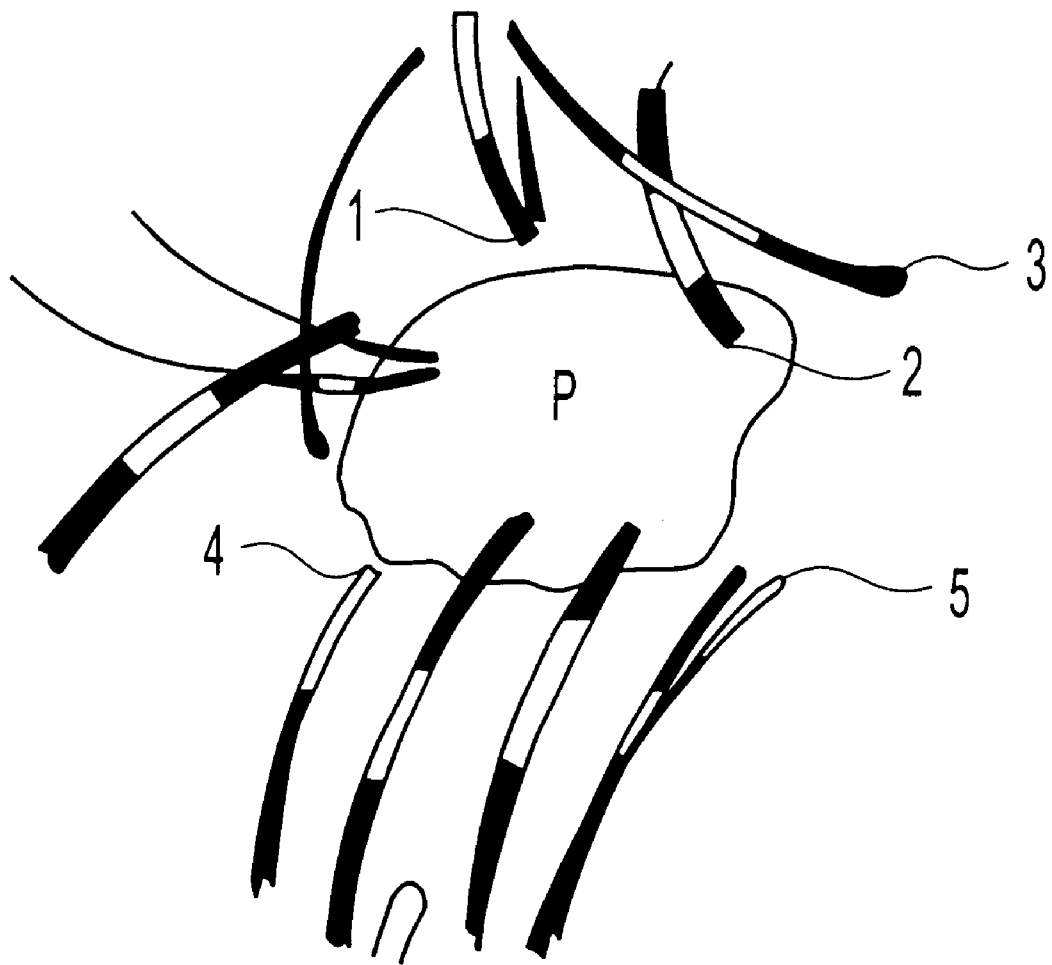
Figure 4:
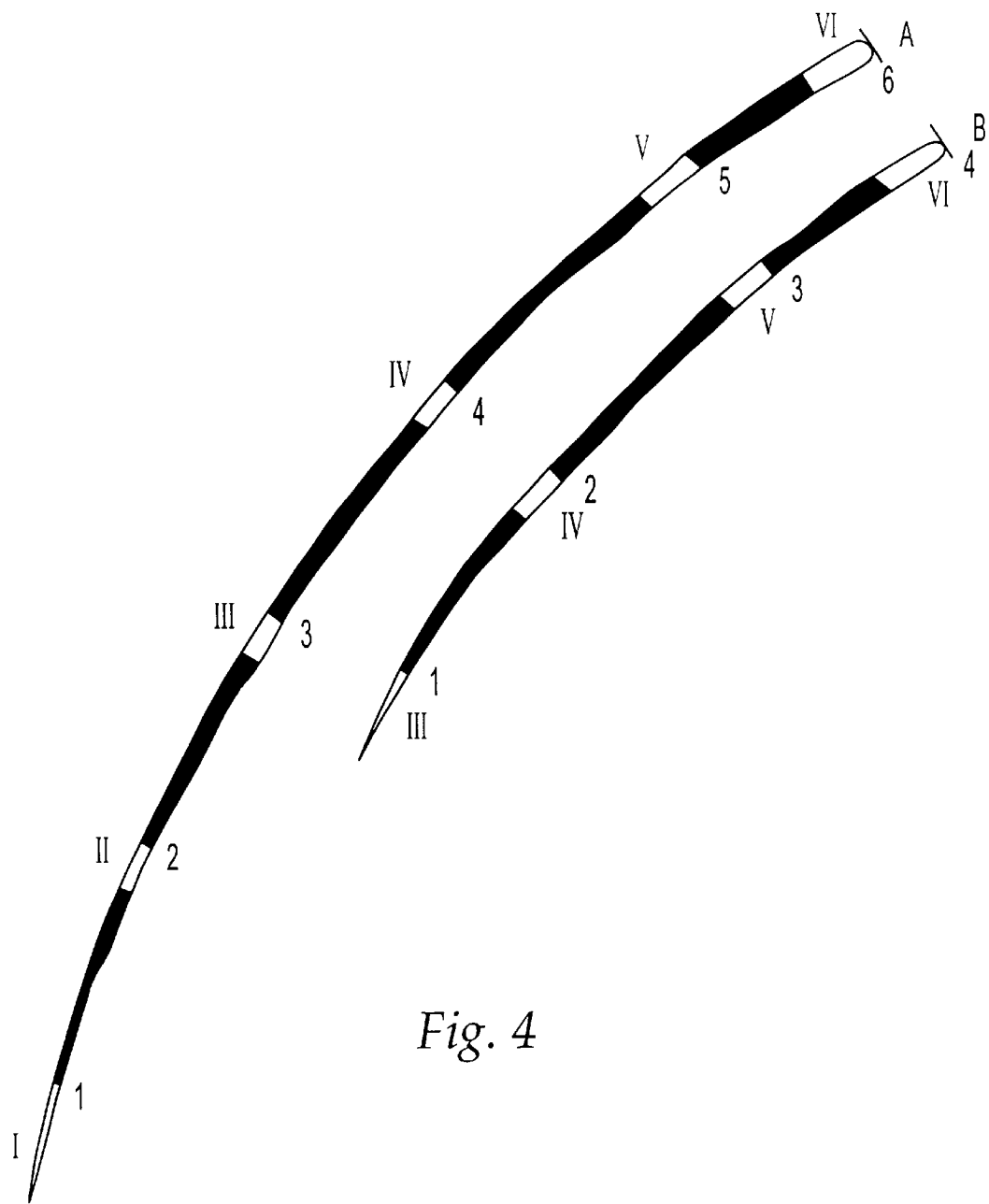

The present invention relates to the method of measuring many parameters of hair quality such as a diameter size of hair shaft, the rate growth of each hair shaft, the total time in each phase of hair crowing cycle. The method can be done repeatedly to observe the dynamic changes of these parameters of which the method then can be used to study the change of these hair parameters affected by foods, drug, certain products, activities and habits.

2. Description of Related Art

Hair problems and diseases, particularly thinning hairs and furs, are very common in both human and animals. Thin hairs and furs presumably are caused by many specific changes of hair growth cycle. If a high percentage of hairs or furs on the body part of interest is not performing the function of growing out hair shafts, those hairs and furs are in resting or catagen phase of hair cycle. The resting hairs will fall out in very near future, at this stage the hairs or furs will not grow further if one shaves the area. Left over hair follicles after the shedding of hair shafts will grow new hair shaft and if the process takes longer times the number of hair shafts per unit area will decrease and cause empty area at the spot. In another case if new hairs can grow out immediately but the new hairs are generating hair shafts with a significantly slow speed, then the new hairs will not match the surrounding normal hairs in length which will give the appearance of thinning hairs. The size of hair shafts also determine the look of either thick or thin hairs since larger hair shaft will either reflect or absorb light, depending on the color of the hair, better than hair with small diameter shaft. The ability of each hair follicle to generate more than one hair shaft at a time will also give more amount of hair on the area. All of the parameters regarding to the generated hair shafts should be measured during the anagen or growing phase of hair cycle. The steady growth rate of each hair shaft is also important to achieve the smooth silky hair and fur. Finally the total duration of growing phase will dictate when each hair will cease growing and return into resting phase before fall out to complete the whole cycle. Any factors possibly force the hair root to cease growing will shorten the duration of this growing phase and automatically increase the number of hairs getting into resting phase as early mentioned. If there is any versatile method being able to measure the percentage of growing hair shafts and non-growing or non-performing hair shafts, to calculate the approximate time of new hair to grow out from the empty follicles, to measure the rate of generating hair shaft among all of the growing ones, to count the total number of hair density in the area, to measure the size of all the hair shafts in the observed unit field and finally to monitor all the changes of these parameters through the whole duration of growing time, resting period and falling phase the outcome of these data will benefit many people. Medical doctors will be able to classify human hair problems more accurately and based on pathophysiological basis. Veterinarian will understand how to improve the nature of furs both in normal and ill animals. Food and drug industries can use the method to study many potential food supplements, herbal products and drums possibly influencing on each specific quality of hair through the whole cycle. Meticulously combining many factors with clear effects but with different roles will enhance the significant results of making good healthy hairs and furs. The method also can be used to identify the negative effects of other foods, products, drugs, activities and habits common to people and animals in daily life of which the information will help the related industries upgrade and improve the qualities of their products mentioned to benefit the consumers. Government can use the method to screen cosmetic hair care products and hair styling device for safety and benefits of people. However, the fact is there are still no methods that can have the capability as mentioned.

Available methods being used currently can calculate the percentage of growing hair shafts versus non-growing portion but the methods require the examined body part to be shaved and observed several days later. The methods can not be used on unshaved area and dose not have the novelty to reach any conclusion on the duration of hair growth cycle necessary as stated in the previous paragraph. Also any changes of hair shaft diameter size and growing rate through time on the same hair shaft can not be measured and recorded. Although hair density measuring method is also available with specific device obtaining the photo or image for manual counting, the method can not give information of how the hair density has changed. To be precise, all available methods also can not closely observe and record the dynamic changes of all the parameters through out its life cycle.

Moreover, all the available methods are not practically helpful on the daily basis application to benefit people who intend to use or to be used such as the practice in medical office.

SUMMARY OF THE INVENTION

A new method of measuring most of parameters required to evaluate the complete quality of human and animal hairs in the observed area is invented. This new invention will give the results of following:

1. The exact percentage of non-growing hairs versus growing ones in the area of measuring.
2. The approximate gap time of individual hair follicle between the point of hair shedding and the early sign of regenerating a young tip of new hair shaft.
3. The rate of individual hair shaft being produced per day at any point in time through its whole life cycle.
4. The diameter size of each hair shaft correlating with the data in 3.
5. The amount of hair moving into and out of resting phase each month.
6. The total growing duration of an individual hair starting from the early day until it transcends into the resting phase.
7. The total time of a hair staying in the non-growing phase before being sheded out.
8. The budding activities of a follicle to give more than one hair shaft per follicle.
9. The dynamic changes of each hair shaft parameters in the same follicles mentioned in 8.

All the results can be recorded and retrieved for further statistic calculations and comparisons to see the effects of many unknown and known factors ranging from foods, drugs, hair care products, activities and habits on the health and quality of hair.

DETAILS OF THE INVENTION

A specific site of skin at the body part, with hairs for studies is selected by giving the priority to the area with natural pigmented lesions such as nevi, moles, lentigenes, seborrheic keratosis, telangiectasia. These lesions can be easily located each time when we need to re-exam the changes of all the hair quality parameters. Also the small lesion (P) easily identified in the field of exam can help orientating the specific location of each hair follicle as seen in drawing 1. This simple technique will give the good opportunity for the observer to see the specific changes of each identified hair shaft through time of hair measuring. Without any preparation the scalp with the natural marker as perfect indicator will provide the information of hair density, hair size and the rough estimation of whether an individual hair is growing or not by comparing the actual pictures of the spot over time as drawing 2. Follicle 1 showed the new hair tip generating out of the well-established hair shaft. Follicle 2 showed the disappearing of the previous hair shaft. Follicle 3 showed the change in hair shaft diameter size. The attempt to use this natural marker as a simple and good indicator for the mentioned advantages has never been observed and brought into practice. However, in the case that not having any natural marker to work with, the photo at either the top or lateral view of scalp is taken for being used as a map to identify the approximate spots being examined. A few areas are chosen for examinations since the more data available the more accuracy it will gain in analyzing step using basic statistic calculation.

The invention method also includes a simple hair dying step. Several colors of hair dye creams and bleaching solutions easily found in supermarket are used, with small amount such as 0.3 ml per measured area. The selected dye with specific color (brown, blue, green, red etc.) permanently stains the hair shaft after about an hour application (exact time being previously calibrated as later detailed). The area then is washed with shampoo or simply wiped clean. The area is seen through electronic camera device with enough magnifying power to observe the stained area. Successfully decolorizing of all the hair shafts at the point of hair shaft growing out of the skin is the final of this step (also it will help calibrating the exact time of decolorizing step depending on different brands of the dye and colors). Twenty four to one hundred sixty eight hours (1–7 days) later the same area then is viewed under the camera and the image is captured under the observer's supervision. The angle of the camera will be adjusted until the new image has the similar orientation of all the hairs surrounding the marker as seen in previous images stored during the first examination: In drawing 3 representing the new image, there are some hairs with natural hair color growing out of the subject's skin with varieties of their length as seen in follicle number 1, 2 and 3. A number of them are still demonstrating the color of the selected dye stained on as viewed during the end of the dying step (follicle number 4 and 5). From this data, a percentage of growing hairs and non-performing hairs can be recorded for future comparison. To calculate the growing rate of each hair shaft, the length of each hair shaft with normal hair color must be measured one by one. The data is subjected to mathematics calculation by using the magnifying power of the recording camera and the total amount of time gap between the time point of completing the dying step and the time point of having the dyed area measured again. This can be done manually or automatically by having the prepared table or mathematics program containing the result of the known equation that can find the actual grove rate. The growth rate is equal to the measured length (millimeter or inch) obtained from the image divided by the multiplying value of magnifying factor and the time gap (recorded in hours or days). Entering the obtained data into the normal statistical calculating practice can derive to the value of the maximum, the minimum, the mode, the median of the whole area growth rate with standard deviation and variance. The value will be used to compare with the other value obtained either from the same area but different time or to compare with the value obtained from the different area to reach the conclusion whether there is significant changes of hair growth rate. Also following the dynamic changes of individual non growing hairs until each of them fall out will give the duration of time between the starting time of resting phase and the day they shedding out. During this period a manual technique or device to gently pull those hairs to specify the point of time of hair root loosed the attachment and ready to fall out is included. Once the follicles have emptied the hair threads, continuously following the spots to see when the tip of new hairs is starting to grow out of the follicles. The time gap taken to see the tip of hair being generated out is recorded and represents the total time of this segment of hair cycle. During this step there is another benefit of this invention as following. After the exams to gather data of non-growing hair percentage, the observer can weekly observe the progressing change of this percentage by seeing the decrease amounts of previous stained color hair shafts at the junction of those hair shafts and the skin. The decrease number of stained hairs mentioned in the last sentence should equal to the amount of hairs falling out of the examined area. However, the left over stained hairs are not representing the total amount of hairs resting in the area since some of the unstained shafts may already cease to grow at any time during this step of viewing. The viewing only provide the fact that how many resting hairs from the previous observation are either left over or pushed out before the new examination will be carried on. This information will help interpreting the result from the new round of staining test to gain the fact that how many non-growing hairs are the new ones recently moving into the resting phase. By doing this type of observation the dynamic changes of the hairs moving into and out of the resting phase can then be measured quite accurately. The amount of total hairs moving into the resting phase at a specific range of time will be important for further analysis. Monitoring the lone percentage of the non-growing hairs in the area at any point in time then can be specify more in details by using this step of approach. This technical step can provide the result of:

1. dynamic change of the hairs moving into and out of the resting phase
2. a right answer of whether, if the amount of hair in resting phase has increased, the amount of hairs moving into the resting phase is more or the amount of hairs moving out of the resting phase is less
3. a hologram demonstrating the amount of hair moving or shedding out as seen in x axis and how frequently the area has shed out the hair as seen in y axis. Total benefits of this simple dying technique in this invention is not available before and there is not any current technique that can out perform this simple invention regarding to these benefits.

Not only the benefits of finding the approximate time of the hair cycle starting from the ceasing point of hair growth to the point of falling and the time spent in generating the new tip of hair out of the empty follicle. But also the invention has the capability to measure the total growing time starting from the date of new hair tipping out of its under skin follicle to the day it ceases to grow which is another important phase of the whole cycle of an individual hair. Choosing several colors of hair dye, recording the sequence of the colors and exact date planned to be used in this step of the invention. Staining the hair shaft as mentioned in previous paragraph, among these hair follicles, a few new hairs just entering the growing phase will tip out of the new reform hair follicles. The color will stain both the shafts of old hairs and the tip of new hairs. The color stained at the tip will tell the observer when it was stained. Each color using will have it own date record. Consequently the similar area is subjected to the dying step monthly, every two months, quarterly or biannually depending on the protocol relying on the status of growth rate obtained from the first measuring and how wide the segment of hair shaft being stained each time. But each time of new dying has to use the planned sequence of colors prepared for the whole method and each dye should be at least separated enough by natural color hair shaft. With successful process, in drawing 4, the segment of the color dyed hair shaft will switch with the natural color band obviously. By repeating the similar step of staining and waiting periodically as planned, any fallen hair will have the zebra bands of artificial colors switched with natural color on the whole length of the hair thread. The artificial colors will arrange on the whole range of the hair thread specifically as planned (I, II, III, IV, V and VI). Collecting all the hairs with its tip stained, measuring each segment of natural color from point 1 to point 2, point 2 to point 3, point 3 to the end of the hair root. The measuring will go on from the first segment till the end of hair root, no matter how many bands there are on each hair specimen. Hair A has six segments stained with color I to color VI while hair B has only three segments stained with color III to color VI. The distance between point 1 and point 2 timed with the rate of growth of the segment will give the duration of time it spends to generate it. Simple adding all the data obtained from each segment calculating will then gives the total approximated duration of growth of that specific hair. In a different approach, once the hair with stained tip cease growing, cutting the hair for similar measuring will give more specific time of growing phase, not including the total time of resting. Naturally, in the same area, each new hair grows out at different time. However, hairs with similar tip color are assumed to grow out at the same time. Color at the tip of each hair then is logically representing each hair group growing out form the same area but at different time frame. Further comparing the duration of growth of each hair group will give the valuable insight whether there is any improvement of hair quality regarding to the total duration of growth. The invention of producing the unique hair specimens described for measuring the total duration of growth will help specifying the information obtained from the previous step mentioned in paragraph 2. No similar technique has ever been mentioned to provide the opportunity to study the quality of hair in this dimension.

To capture all mentioned images, electronic camera such as A 71-50N Scarlar CCD scanner (Scalar corporation 3-28-6 yoyogi shibuya-ku Tokyo, Japan) is used to obtained the still electronic images. The still images then are transferred through either Asymetrix Digital Video Producer Capture version 5.0 (www. asymetrix.com) or Aver (AverMedia Technologies, Inc) to the Microsoft window bitmap paint program. Both window 3.11 version and window 95 version are used to store the images. The images then can be archived and retreived for measuring to reach the data. Statiscal analysing program such as SPSS program (SPSS .co) is used to calculate.

What is claimed is:

1. A method for measuring the quality of hairs, the method comprising the steps of:

a. identifying a viewing area of skin from a part of a body for which hair quality measurement is desired;

d. viewing the viewing area with an apparatus to create first images of the area comprising hair shafts coming out of the area and storing the first images for further comparison;

e. dying the hair shafts with coloring products;

f. viewing the viewing area with the apparatus to create second images including a change of hair color at selected points of each hair shafts coming out of the skin including any new hairs with tips coming out, and storing the second images;

g. viewing the viewing area again 1 to 7 days after the dying step with the apparatus to create third images which identify the changes of each hair shafts after dying and growing;

h. retrieving the first, second and third images, and measuring the size of each hair shaft coming out of the skin in the first image, numbering each hair shaft in the viewing area in the first image, and counting the total hair shaft density being measured in the first image;

i. counting separately the amount of hair shafts with either a natural hair color or the dyed color at a point where the hair comes out from the skin from the third images, and measuring segments of natural hair color on the hair shafts in the third image to create hair growth data;

j. statistically analyzing the hair growth data obtained from the preceding steps to summarize the hair growth data;

k. pulling non-growing hairs and viewing the area where the non-growing hairs were pulled periodically to capture the image of the hairs at the time of shedding, and recording the shedding date;

l. viewing the viewing area weekly for about 4 weeks to monitor the amount of dyed hair shafts in the third images;

m. repeating steps e to l to monitor the monthly progress of hair quantity and quality;

n. viewing the viewing area to monitor any new hair growth in any areas where non-growing hairs were pulled and recording such hair growth data for further calculation;

o. repeating the dying steps from step e to step h, using a different color in planned sequence to create different color bands and creating sets of first, second and third images and using the sets of images for growth rate calculation;

p. collecting a plurality of hairs in step o with different color bands and measuring and calculating to determine the growth rate and the length of each band.

2. A method according to claim 1, wherein one of a natural pigmented marker is selected or an artificial marker is applied on an identified area on the body part to be measured, said identified area being the viewing area.

3. A method according to claim 2, wherein the artificial marker is applied mechanically or electronically to mark the viewing area.

4. A method according to claim 1, wherein the coloring products can be any shades of colors that can differentiate from the natural hair color.

5. A method according to claim 1, wherein the dyeing step involves using fluorescence dyes as the coloring products.

6. A method according to claim 1, wherein the apparatus is a camera, and the camera can magnify the observed hairs in any range of power.

7. A method according to claim 6, wherein the camera is one of electronic, conventional, or digital.

8. A method according to claim 1, further comprising a device with capability of automatically matching the first, second, or third images and storing the images.

9. A method according to claim 8, wherein the images can be stored in any using specific computer software programs to store, archive and retrieve all the stored images for further statistic calculations.

10. A method according to claim 9, wherein the data are used to create new mathematically statistically analyzed figures.

11. A method according to claim 10, wherein the mathematically statistically analyzed figures are used to conclude the outcome of the quality of hairs being measured.

12. A method according to claim 1, further comprising repeating steps d through p on one of a monthly or yearly basis.

13. A method according to claim 12, further comprising reaching a conclusion regarding the rate of hair growth including the total time and activities of growing (anagen), resting (catagen) and falling (telogen) of hair.

14. A method according to claim 13, further comprising utilizing the conclusion to confirm the effects of any types of foods, drugs, products, devices, activities and habits on the hair quality and to identify new diseases and hair problems.

15. The method according to claim 14, wherein the predetermined time is 1 to 7 days.

16. The method according to claim 14, further comprising repeating the dying step with a different colored coloring product and repeating the viewing steps to create the second and third images and utilizing the first, second, and third images to compute any changes in hair growth.

17. The method according to claim 16, wherein the preselected period is at least one of months and years.

18. The method according to claim 14, further comprising repeating the steps on the method for the viewing area after a preselected period and utilizing the data obtained from the steps to draw conclusions regarding hair growth.

19. A method according to claim 1, further comprising measuring the length of the bands and the diameter of the hair shaft of the pulled hairs with multiple bands of color.

20. A method according to claim 1, further comprising reaching a conclusion regarding the rate of hair growth including the total time and activities of growing (anagen), resting (catagen) and falling (telogen) of hair.

21. A method according to claim 20, further comprising utilizing the conclusion to confirm the effects of any types of foods, drugs, products, devices, activities, and habits on the hair quality and to identify new diseases and hair problems.

22. The method according to claim 1, wherein the pigmented marker is at least one of nevi, lentigenes, freckles, telangiectasia, seborrheic keratosis, or tattooed marks.

23. A method for measuring the quality of hairs, the method comprising the steps of:

identifying an area of skin from a part of a body for which hair quality measurement is desired, viewing a viewing area with an apparatus to create first images of the viewing area comprising hair shafts coming out of the viewing area and storing the first images for further comparison, dying the hair shafts with coloring products, viewing the viewing area with the apparatus to create second images including a change of hair color at selected points of each hair shafts coming out of skin including any new hairs with tips coming out, and storing the second images, viewing the viewing area again after a predetermined time with the apparatus to create third images which identify the changes of each hair shafts, retrieving the first, second and third images, and using computer programs to compute any changes in hair growth.

* * * * *